(12) United States Patent
Zou et al.

(10) Patent No.: US 10,400,193 B2
(45) Date of Patent: Sep. 3, 2019

(54) 2,4,7-TRIMETHYLOCT-6-EN-1-OL AS FRAGRANCE INGREDIENT

(71) Applicant: GIVAUDAN SA, Vernier (CH)

(72) Inventors: Yue Zou, Jiangsu (CN); Andreas Goeke, Winterthur (CH); Dominique Lelievre, Kindhausen (CH); Jie Liu, Jiangsu (CN)

(73) Assignee: GIVAUDAN S.A., Vernier (CH)

( * ) Notice: Subject to any disclaimer, the term of this patent is extended or adjusted under 35 U.S.C. 154(b) by 49 days.

(21) Appl. No.: 15/746,320

(22) PCT Filed: Jul. 27, 2016

(86) PCT No.: PCT/EP2016/067941
§ 371 (c)(1),
(2) Date: Jan. 19, 2018

(87) PCT Pub. No.: WO2017/017152
PCT Pub. Date: Feb. 2, 2017

(65) Prior Publication Data
US 2018/0201872 A1 Jul. 19, 2018

(30) Foreign Application Priority Data

Jul. 27, 2015 (WO) ............... PCT/CN2015/085160

(51) Int. Cl.
| | |
|---|---|
| *C11D 3/50* | (2006.01) |
| *C11B 9/00* | (2006.01) |
| *A61K 8/34* | (2006.01) |
| *A61Q 5/02* | (2006.01) |
| *A61Q 13/00* | (2006.01) |
| *C07C 33/025* | (2006.01) |

(52) U.S. Cl.
CPC ............ *C11B 9/0015* (2013.01); *A61K 8/342* (2013.01); *A61Q 5/02* (2013.01); *A61Q 13/00* (2013.01); *C07C 33/025* (2013.01); *C11D 3/50* (2013.01)

(58) Field of Classification Search
CPC ........................... C07C 33/025; C11B 9/0015
See application file for complete search history.

(56) References Cited

U.S. PATENT DOCUMENTS

| | | | |
|---|---|---|---|
| 3,463,818 A | 8/1969 | Blumenthal | |
| 3,882,156 A * | 5/1975 | Henrick | ................ C07C 33/048 558/182 |
| 3,919,324 A * | 11/1975 | Himmele | ................ C07C 45/49 512/27 |
| 2010/0069508 A1 | 3/2010 | Bajgrowicz | |
| 2017/0113988 A1* | 4/2017 | Foley | ..................... C07C 29/36 |

FOREIGN PATENT DOCUMENTS

| | | |
|---|---|---|
| CN | 102295531 A | 12/2011 |
| EP | 1762565 A1 | 3/2007 |
| WO | 2012160189 A1 | 11/2012 |

OTHER PUBLICATIONS

International Search Report and Written Opinion of the International Searching Authority for corresponding application PCT/EP2016/067941 dated Oct. 7, 2016.
International Search Report and Written Opinion of the International Searching Authority for corresponding application PCT/CN2015/085160 dated Apr. 29, 2016.

* cited by examiner

*Primary Examiner* — John R Hardee
(74) *Attorney, Agent, or Firm* — Norris McLaughlin, PA

(57) ABSTRACT

2,4,7-Trimethyloct-6-en-1-ol which is useful as a fragrance ingredient.

11 Claims, No Drawings

2,4,7-TRIMETHYLOCT-6-EN-1-OL AS FRAGRANCE INGREDIENT

This is an application filed under 35 USC 371 based on PCT/EP2016/067941, which in turn is based on PCT/CN2015/085160 filed 27 Jul. 2015. The present application claims the full priority benefit of these prior applications and herein incorporates by reference the full disclosures of these prior applications.

The present invention relates to 2,4,7-trimethyloct-6-en-1-ol. This invention relates furthermore to their use as high blooming fragrance ingredient and to fragrance compositions and perfumed products comprising it. It furthermore relates to a method of its production.

Fragrances possessing a "bloom" are of high interest in the fragrance industry, mainly because bloom is a generally pleasant, surprising sensory effect signalizing a powerful perfume. This sensory effect provides the customer an immediate sensation, such as an impression of scenting efficiency or freshness. The bloom can be thought of as a signature fragrance accord of a perfumed product and is therefore an important characteristic which strongly influences consumer acceptance of a perfumed product. Accordingly, there is an increasing demand in the fragrance industry for fragrances possessing a blooming effect.

To the best of our knowledge, 2,4,7-trimethyloct-6-en-1-ol (I) has never been described in literature. The structurally closest analogue is 2,4,7-trimethylocta-2,6-dien-1-ol (A), reported in WO2012160189 having a significantly different odor profile.

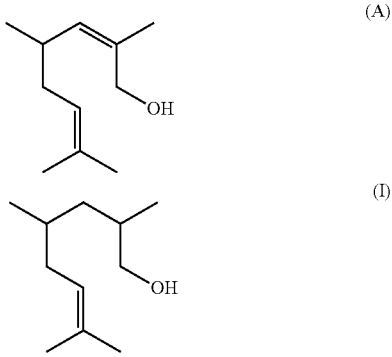

Whereas 2,4,7-trimethylocta-2,6-dien-1-ol (A) is described possessing a floral, rosy odor note, with some geranium citrus-like side notes, 2,4,7-trimethyloct-6-en-1-ol (I) possess a clear main citrus odor character with a clear green grapefruit/rhubarb connotation.

Beside its odour profile, as described above, surprisingly it was found that 2,4,7-trimethyloct-6-en-1-ol (I) enhances the freshness and cleanliness attributes of a perfumed product to which it is added without changing the overall odor profile of the perfumed product. As an example, one may cite the addition of 2,4,7-trimethyloct-6-en-1-ol (I) to a Fougère fragrance, resulting in a fragrance accord which will be fresher but remains to be a Fougère in character, and will not change the citrus, herbaceous, green, floral and animalic soul of the accord, which generally characterize this type of perfume (Fougère fragrance accords).

What is even more surprising is, that whereas 2,4,7-trimethylocta-2,6-dien-1-ol (A) does not have a bloom, 2,4,7-trimethyloct-6-en-1-ol (I) is a highly blooming fragrance ingredient.

A fragrance "bloom" refers to the short term impact of an ingredient at a certain distance from the fragrance source. Short term means a few seconds to a few minutes after an external action has been applied to the fragrance ingredient itself. Such an action (or event) can be multiple in nature. Opening a fragrance flask, spraying a fragrance solution in the air or on the skin, contacting a perfumed product with a surface or with water, and in particular diluting a perfumed product with water, are typical actions capable of inducing a bloom. Both, perfumes and individual fragrance ingredients, can be classified in low blooming to high blooming perfume/fragrance ingredient, whereas a high bloom is highly desired by consumers in the today market place.

Although "bloom" is typically a time-dependent dynamic performance attribute of a fragrance it is measured after a certain time, but not later than 30 minutes, preferably 15 to 20 minutes, after the action has taken place. Typically, the assessment is performed in a closed volume of air, for example in a non-ventilated booth. Typically a panelist performs the assessment by smelling a certain volume of air (e.g. one or two breaths) in the booth through a small window which is open only during the assessment. Typically, the window is located between 0.5 meter and 2 meters apart from the source, preferably between 0.8 meter and 1.5 meter, for example 1.3 meter. The exact geometry of the experimental set-up is not critical, but it must be reproducible from one assessment to the other.

All the attributes mentioned above, taken together, make 2,4,7-trimethyloct-6-en-1-ol highly desirable for the fragrance industry.

Thus, there is provided in a first aspect 2,4,7-trimethyloct-6-en-1-ol, and its use as fragrance. 2,4,7-Trimethyloct-6-en-1-ol may be used in its diasteriomerically pure forms (syn-2,4,7-trimethyloct-6-en-1-ol; anti-2,4,7-trimethyloct-6-en-1-ol) or in a mixture of diastereomers, e.g. in a ratio of 80:20 to 20:80, such as 60:40 to 40:60 mixtures, including 1:1, 1:1.5, 7:3 and 3:7 mixtures.

In a further aspect there is provided a fragrance composition or perfumed product comprising 2,4,7-trimethyloct-6-en-1-ol (which includes 2,4,7-trimethyloct-6-en-1-ol in its diasteriomerically and/or enantiomerically pure forms or in a mixture of diastereomers and/or enantiomers).

In one embodiment there is provided the use as fragrance of 2,4,7-trimethyloct-6-en-1-ol enriched in rel. (2S,4S)-2,4,7-trimethyloct-6-en-1-ol (i.e. syn-2,4,7-trimethyloct-6-en-1-ol).

In another embodiment there is provided the use as fragrance of 2,4,7-trimethyloct-6-en-1-ol enriched in rel. (2S,4R)-2,4,7-trimethyloct-6-en-1-ol (i.e. anti-2,4,7-trimethyloct-6-en-1-ol).

In a further aspect there is provided a method of imparting freshness and cleanness to a perfumed product, said method comprising the step of incorporating 2,4,7-trimethyloct-6-en-1-ol into said perfumed product.

2,4,7-Trimethyloct-6-en-1-ol may be added directly to the product or may admixed with other known fragrance ingredients resulting in a fragrance composition, and then added to the product.

The following list comprises examples of known fragrance ingredients, which may be combined with 2,4,7-trimethyloct-6-en-1-ol:

essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;

alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;

aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl)ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl)ethanone); Isoraldeine® ((E)-3-methyl-4-(2,6,6-trimethylcyclohex-2-en-1-yl)but-3-en-2-one); Hedione® (methyl 3-oxo-2-pentylcyclopentaneacetate); 3-(4-isobutyl-2-methylphenyl)propanal; maltol; methyl cedryl ketone; methylionone; verbenone; and/or vanillin;

ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo[4.1.0]heptane-2,5-[1,3]dioxane]);

esters and lactones, e.g. benzyl acetate; cedryl acetate ((1S,6R,8aR)-1,4,4,6-tetramethyloctahydro-1H-5,8a-methanoazulen-6-yl acetate); γ-decalactone (6-pentyltetrahydro-2H-pyran-2-one); Helvetolide® (2-(1-(3,3-dimethylcyclohexyl)ethoxy)-2-methylpropyl propionate); γ-undecalactone (5-heptyloxolan-2-one); and/or vetiveryl acetate ((4,8-dimethyl-2-propan-2-ylidene-3,3a,4,5,6,8a-hexahydro-1H-azulen-6-yl) acetate);

macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

Further examples of known fragrance ingredients with which 2,4,7-trimethyloct-6-en-1-ol may be combined include 6-methoxy-2,6-dimethylheptan-1-al (Methoxymelonal); 5,9-dimethyl-4,8-decadienal (Geraldehyde); octahydro-8,8-dimethylnaphthalene-2-carbaldehyde (Cyclomyral); 5-methyl-2-(1-methylbutyl)-5-propyl-1,3-dioxan (Troenan); 3,7,11-trimethyldodeca-1,6,10-trien-3-ol (optionally as an isomeric mixture) (Nerolidol); 2-methyl-4-phenylbutan-2-ol (dimethylphenylethylcarbinol); 1-(1-hydroxyethyl)-4-(1-methylethyl)cyclohexane (optionally as a mixture of the diastereoisomers) (Mugetanol); (4-methyl-3-pentenyl)cyclohexenecarbaldehyde (Citrusal); 3-(p-(2-methylpropyl)phenyl)-2-methylpropionaldehyde (Silvial); 3-p-cumenyl-2-methylpropionaldehyde (Cyclamenaldehyde); and mixtures of: cis-tetrahydro-2-isobutyl-4-methylpyran-4-ol and trans-tetrahydro-2-isobutyl-4-methylpyran-4-ol.

Even further examples of known fragrance ingredients may include Amyl Salicylate (pentyl 2-hydroxybenzoate); Aurantiol® ((E)-methyl 2-((7-hydroxy-3,7-dimethyloctylidene)amino)benzoate); Benzyl Salicylate (benzyl 2-hydroxybenzoate); Cis-3-hexenyl Salicylate ((Z)-hex-3-en-1-yl 2-hydroxybenzoate); Citronellyl Oxyacetaldehyde (2-((3,7-dimethyloct-6-en-1-yl)oxy)acetaldehyde); Cyclemax (3-(4-propan-2-ylphenyl)propanal); Cyclohexyl Salicylate (cyclohexyl 2-hydroxybenzoate); Cyclomyral® (8,8-dimethyl-1,2,3,4,5,6,7,8-octahydronaphthalene-2-carbaldehyde); Cyclopentol (2-pentylcyclopentan-1-ol); Cymal (4-(4-hydroxy-4-methylpentyl)cyclohex-3-enecarbaldehyde); Dupical ((E)-4-((3aS,7aS)-hexahydro-1H-4,7-methanoinden-5(6H)-ylidene)butanal); Floral Super ((4E)-4,8-dimethyldeca-4,9-dienal); Florhydral® (3-(3-isopropylphenyl)butanal); Florol® (2-isobutyl-4-methyltetrahydro-2H-pyran-4-ol); Gyrane (2-butyl-4,6-dimethyl-3,6-dihydro-2H-pyran); Hexyl Salicylate (hexyl 2-hydroxybenzoate); Helional (3-(1,3-benzodioxol-5-yl)-2-methylpropanal); Lyral® (4-(4-hydroxy-4-methylpentyl)cyclohex-3-enecarbaldehyde); Majantol® (2,2-dimethyl-3-(m-tolyl)propan-1-ol); Mayol® ((4-isopropylcyclohexyl)-methanol); Melafleur (8,8-dimethyl-2,3,4,5,6,7-hexahydro-1H-naphthalene-2-carbaldehyde); Melonal (2,6-dimethylhept-5-enal); Muguesia (3-methyl-4-phenylbutan-2-ol); Muguet alcohol (3-cyclohexyl-2,2-dimethylpropan-1-ol); Verdantiol ((E)-methyl 2-((3-(4-(tert-butyl)phenyl)-2-methylprop-1-en-1-yl)amino)benzoate); Peonile (2-cyclohexylidene-2-phenylacetonitrile); Phenoxanol® (3-methyl-5-phenylpentan-1-ol); Rossitol® (3-isobutyl-1-methylcyclohexanol); Suzaral (2-methyl-3-[4-(2-methylpropyl)phenyl]propanal); Muguol® (3,7-dimethylocta-4,6-dien-3-ol); Tetrahydro Linalool (3,7-dimethyloctan-3-ol); Acalea ((2E)-2-[(4-methylphenyl)methylidene]-heptanal); Dihydro IsoJasmonate (methyl 2-hexyl-3-oxocyclopentane-1-carboxylate); Hexyl Cinnamic Aldehyde ((E)-2-benzylideneoctanal); Acetoin (3-hydroxybutan-2-one); Adoxal (2,6,10-trimethylundec-9-enal); Aldolone® (7-propyl-2H-1,5-benzodioxepin-3(4H)-one); Ambrocenide® ((4aR,5R,7aS,9R)-Octahydro-2,2,5,8,8,9a-hexamethyl-4H-4a,9-methanoazuleno[5,6-d]-1,3-dioxole); Ambroxan (3a,6,6,9a-tetramethyl-2,4,5,5a,7,8,9,9b-octahydro-1H-benzo[e][1]benzofuran); Bacdanol® ((E)-2-ethyl-4-(2,2,3-trimethylcyclopent-3-en-1-yl)but-2-en-1-ol); Calone 1951® (7-methyl-2H-benzo[b][1,4]dioxepin-3(4H)-one); Cetalox® (3a,6,6,9a-tetramethyl-2,4,5,5a,7,8,9,9b-octahydro-1H-benzo[e][1]benzofuran); Cinnamic alcohol ((E)-3-phenylprop-2-en-1-ol); Citral ((E)-3,7-dimethylocta-2,6-dienal); Cyclabute ((3aR,6S,7aS)-3a,4,5,6,7,7a-hexahydro-1H-4,7-methanoinden-6-ylisobutyrate); Cyclacet™ ((3aR,6S,7aS)-3a,4,5,6,7,7a-hexahydro-1H-4,7-methanoinden-6-yl acetate); Cyclaprop ((3aR,6S,7aS)-3a,4,5,6,7,7a-hexahydro-1H-4,7-methanoinden-6-yl propionate); Cyclohexadecanolide; Cyclohexadecenone; Cyclopentadecanone; Delta Damascone ((E)-1-(2,6,6-trimethylcyclohex-3-en-1-yl)but-2-en-1-one); Elintaal Forte (3-(1-ethoxyethoxy)-3,7-dimethylocta-1,6-diene); Ethyl Vanillin (3-ethoxy-4-hydroxybenzaldehyde); Exaltenone ((4Z)-cyclopentadec-4-en-1-one); Floralozone (3-(4-ethylphenyl)-2,2-dimethylpropanal); Fructalate (diethyl cyclohexane-1,4-dicarboxylate); Habanolide ((E)-oxacyclohexadec-12-en-2-one); Galaxolide (4,6,6,7,8,8-hexamethyl-1,3,4,6,7,8-hexahydro-cyclopenta[g]isochromene); Hydroxyambran®

(2-cyclododecylpropan-1-ol); Myraldene (4-(4-methylpent-3-en-1-yl)cyclohex-3-enecarbaldehyde); Jasmal (3-pentyltetrahydro-2H-pyran-4-yl acetate); Javanol® ((1-methyl-2-((1,2,2-trimethylbicyclo[3.1.0]hexan-3-yl)methyl)cyclopropyl)methanol); Lauric Aldehyde (Dodecanal); Mefranal (3-methyl-5-phenylpentanal); Muscenone ((Z)-3-methylcyclopentadec-5-enone); Tonalid® (1-(3,5,5,6,8,8-hexamethyl-5,6,7,8-tetrahydronaphthalen-2-yl)ethanone); Nectaryl® (2-(2-(4-methylcyclohex-3-en-1-yl)propyl)cyclopentanone); Norlimbanol (1-(2,2,6-trimethylcyclohexyl)hexan-3-ol); Raspberry ketone (4-(4-hydroxyphenyl)butan-2-one); Pinoacetaldehyde (3-(6,6-dimethylbicyclo[3.1.1]hept-2-en-2-yl)propanal); Romandolide® (acetic acid (1-oxopropoxy)-, 1-(3,3-dimethyl cyclohexyl)ethyl ester); Sanjinol ((E)-2-ethyl-4-(2,2,3-trimethylcyclopent-3-en-1-yl)but-2-en-1-ol); and/or Velvione® ((Z)-cyclohexadec-5-enone).

A fragrance composition need not be limited to the fragrance ingredients listed above. Other fragrance ingredients commonly used in perfumery may be employed, for example any of those ingredients described in "Perfume and Flavour Chemicals", S. Arctander, Allured Publishing Corporation, 1994, IL, USA, which is incorporated herein by reference, including essential oils, plant extracts, absolutes, resinoids, odourants obtained from natural products and the like.

In one particular embodiment, 2,4,7-trimethyloct-6-en-1-ol may be combined with other alcohols, such as dihydromyrcenol, linalool, ethyl linalool, and 6-isopropyl-2,4-dimethylcyclohex-3-en-1-ol (odor description: impactful, green, rooty, earthy, pyrazin-like), and mixtures thereof.

In a further embodiment 2,4,7-trimethyloct-6-en-1-ol may be combined with salicylates, such as amyl salicylate, benzyl salicylate, cis-3-hexenyl salicylate, cyclohexyl salicylate and hexyl salicylate, and/or Hedione® (methyl 3-oxo-2-pentylcyclopentaneacetate), and mixtures thereof.

In a further embodiment 2,4,7-trimethyloct-6-en-1-ol may be combined with 2,4,7-trimethylocta-2,6-dien-1-ol ((E)-2,4,7-trimethylocta-2,6-dien-1-ol and/or (Z)-2,4,7-trimethylocta-2,6-dien-1-ol, [1-methyl-2(5-methylhex-4-en-2-yl)cyclopropyl]-methanol, 2-(2-methyl-2-(3-methylbut-2-en-1-yl)cyclopropyl)propan-1-ol, (2-(1-(2,2-dimethylcyclopropyl)propan-2-yl)-1-methylcyclopropyl)methanol (odor description: floral rosy, sandalwood like), 2,4,7-trimethylocta-3,6-dien-1-ol ((E)-2,4,7-trimethylocta-3,6-dien-1-ol and/or (Z)-2,4,7-trimethylocta-3,6-dien-1-ol), and/or 2,4,7-trimethyloct-7-en-1-ol, and mixtures thereof.

In a further embodiment 2,4,7-trimethyloct-6-en-1-ol may be combined with 2,4,7-trimethylocta-2,6-dien-1-ol ((E)-2,4,7-trimethylocta-2,6-dien-1-ol and/or (Z)-2,4,7-trimethylocta-2,6-dien-1-ol), 2,4,7-trimethylocta-3,6-dien-1-ol ((E)-2,4,7-trimethylocta-3,6-dien-1-ol and/or (Z)-2,4,7-trimethylocta-3,6-dien-1-ol), 2,4,7-trimethyloct-7-en-1-ol, and/or 6-isopropyl-2,4-dimethylcyclohex-3-en-1-ol (e.g., rel. (1R,2S, 6S)-6-isopropyl-2,4-dimethylcyclohex-3-en-1-ol), and mixtures thereof.

In a further embodiment 2,4,7-trimethyloct-6-en-1-ol may be combined with 2,4,7-trimethylocta-2,6-dien-1-ol ((E)-2,4,7-trimethylocta-2,6-dien-1-ol and/or (Z)-2,4,7-trimethylocta-2,6-dien-1-ol), 2,4,7-trimethylocta-3,6-dien-1-ol ((E)-2,4,7-trimethylocta-3,6-dien-1-ol and/or (Z)-2,4,7-trimethylocta-3,6-dien-1-ol), 2,4,7-trimethyloct-7-en-1-ol, and 6-isopropyl-2,4-dimethylcyclohex-3-en-1-ol (e.g., rel. (1R,2S, 6S)-6-isopropyl-2,4-dimethylcyclohex-3-en-1-ol), for example, in a ratio of about 70:14:14:1:1 to about 95:2:2:0.5:0.5.

2,4,7-Trimethyloct-6-en-1-ol may be present in a fragrance composition in any amount, depending on the particular effect that a perfumer wishes to achieve. In a particular embodiment of the present invention, a fragrance composition may contain 2,4,7-trimethyloct-6-en-1-ol in an amount of up to 30% by weight, e.g. 0.2-20% (for example, about 0.5%, 1%, 1.5%, 2%, 3%, 4%, 5%, 6%, 7%, 8%, 9%, 10%, 11%, 12%, 13%, 14%; 15%; 16%; 17%; 18%; 19% by weight) of said composition.

As used herein, "fragrance composition" means any composition comprising 2,4,7 trimethyloct-6-en-1-ol and a base material, e.g. a diluent conventionally used in conjunction with fragrance ingredients, such as diethyl phthalate (DEP), dipropylene glycol (DPG), isopropyl myristate (IPM), triethyl citrate (TEC) and alcohol (e.g. ethanol). Optionally, the composition may comprise an anti-oxidant adjuvant. Said anti-oxidant may be selected from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

2,4,7-Trimethyloct-6-en-1-ol may be used in a broad range of perfumed products, e.g. in any field of fine and functional perfumery, such as perfume, Eau de Parfum, Eau de Cologne, Eau de Toilette, air care products, household products, laundry and fabric care products, body care products and cosmetics. The compounds can be employed in widely varying amounts, depending upon the specific application and on the nature and quantity of other fragrance ingredients. The proportion is typically from 0.001 to 30 (including, e.g., 5, 10, 15, 20, 25) weight percent of the application. In one embodiment, compounds of the present invention may be employed in perfumed products like a fabric softener in an amount of from 0.001 to 0.3 weight percent. In another embodiment, compounds of the present invention may be used in fine perfumery in amounts from 0.1 to 30 weight percent (e.g. up to about 20 weight percent), more preferably between 0.5 and 15 weight percent. However, these values are given only by way of example, since the experienced perfumer may also achieve effects or may create novel accords with lower (e.g. 0.0001 weight % or less based on the perfumed product) or higher concentrations (e.g. 35, 40, 45 weight % or even higher based on the perfumed product).

2,4,7-trimethyloct-6-en-1-ol may be employed in a consumer product base simply by directly mixing 2,4,7-trimethyloct-6-en-1-ol, or a fragrance composition comprising 2,4,7-trimethyloct-6-en-1-ol with the consumer product base, or it may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or it may be chemically bonded to substrates, which are adapted to release the fragrance molecule upon application of an external stimulus such as light, enzyme, or the like, and then mixed with the consumer product base.

Thus, there is provided in a further aspect a method of manufacturing a perfumed product, comprising the incorporation of 2,4,7-trimethyloct-6-en-1-ol, as a fragrance ingredient, either by directly admixing the compound to the consumer product base or by admixing a fragrance composition comprising 2,4,7-trimethyloct-6-en-1-ol, which may then be mixed with a consumer product base, using conventional techniques and methods.

The invention also provides a perfumed product comprising:
 a) as fragrance ingredient at least 2,4,7-trimethyloct-6-en-1-ol; and
 b) a consumer product base.

In a further embodiment it is provided a perfumed product comprising:
 a) as fragrance ingredient at least 2,4,7-trimethyloct-6-en-1-ol;
 b) at least one further fragrance ingredient; and
 c) a consumer product base.

As used herein, 'consumer product base' means a composition for use as a consumer product to fulfil specific actions, such as cleaning, softening, and caring or the like. Examples of such products include fine perfumery, e.g. perfume, Eau de Parfum, Eau de Cologne, and Eau de Toilette; fabric care, household products and personal care products such as laundry care detergents, rinse conditioner, personal cleansing composition, detergent for dishwasher, surface cleaner; laundry products, e.g. softener, bleach, detergent; body-care products, e.g. shampoo, shower gel; air care products and cosmetics, e.g. deodorant, vanishing crème. This list of products is given by way of illustration, and is not to be regarded as being in any way limiting.

The invention is now further described with reference to the following non-limiting examples. These examples are for the purpose of illustration only, and it is understood that variations and modifications can be made by one skilled in the art.

EXAMPLE 1: SYNTHESIS OF 2,4,7-TRIMETHYLOCT-6-EN-1-OL

Method A

A mixture of 2,4,7-trimethylocta-2,6-dien-1-ol (10.1 g, 60.0 mmol) and lithium granules (0.46 g, 66.0 mmol) was heated at 80° C. for 16 hours. The reaction mixture was then allowed to cool to room temperature, diluted with THF (20.0 ml) and quenched with cold water (50.0 ml). The organic layer was separated and the aqueous layer was extracted with ethyl acetate (2×30 mL). The combined organic layers were washed once with brine, and then dried with $MgSO_4$. The solvent was removed on the rotatory evaporator. The crude product was purified by column chromatography (iso-hexane/ethyl acetate, 50:1) and by subsequent Kugelrohr distillation to provide 4.00 g (40%) of 2,4,7-trimethyloct-6-en-1-ol as a colorless odoriferous liquid. B.p. 94° C./0.10 mbar. Two isomers in a ratio of 45:55.

GC/MS (EI), 170 ($M^+$, 3), 151 (1), 137 (2), 123 (2), 112 (20), 96 (42), 83 (75), 69 (62), 55 (100), 41 (59). $^1$H-NMR (300 MHz, $CDCl_3$): δ=5.12 (t, J=7.5 Hz, 1H, $Me_2C$=$CHCH_2$), 3.54-3.35 (m, 2H, $CH_2OH$), 1.99-1.74 (m, 2H, =$CHCH_2$), 1.74-1.66 (m, 1H, =$CHCH_2CH$), 1.70 (s, 3H, $MeCH_3C$=CH), 1.59 (s, 3H, $MeCH_3C$=CH), 1.56-1.49 (m, 1H, $CHCH_2OH$), 1.38-1.09 (m, 2H, $CHCH_2CH$), 0.94-0.83 (m, 6H, $2CHCH_3$) ppm.

$^{13}$C-NMR (75 MHz, $CDCl_3$): δ=132.1, 132.0 (2s, $Me_2C$=CH), 123.2, 123.0 (2d, $Me_2C$=CH), 69.0, 68.3 (2t, $CH_2OH$), 40.6, 40.3 (2t, $CHCH_2CH$), 36.3, 35.0 (2t, $Me_2C$=$CHCH_2$), 33.3, 33.2 (2d, $CHCH_2OH$), 31.0, 30.8 (2d, $Me_2C$=$CHCH_2$), 26.0 (q, $MeCH_3C$=CH), 20.3, 19.2 (q, 4-Me), 17.8 (q, $MeCH_3C$=CH), 17.3, 16.3 (q, 2-Me) ppm.

Odor description: clear main citrus odor character with a clear green grapefruit/rhubarb connotation.

Method B

1) To a 100 mL three-necked flask equipped with a magnetic stirrer and a gas inlet, under argon atmosphere were added Lindlar Pd ($Pd/CaCO_3$ Lead poisoned 0.40 g), (E)-2,4,7-trimethylocta-2,6-dienal (9.00 g, 54.1 mmol) and ethyl acetate (40.0 ml). The reaction mixture was stirred under hydrogen atmosphere at room temperature overnight. The reaction mixture was filtered through a small pad of silica gel and the silica gel was washed with MTBE (2×30 mL). The combined filtrates were concentrated by rotatory evaporator. The crude product was distilled through Kugelrohr to give 2,4,7-trimethyloct-6-enal (8.0 g, 47.5 mmol, 88% yield; boiling point: 80° C./0.15 mbar) as a colorless liquid.

$^1$H NMR (300 MHz, $CDCl_3$): δ=9.59, 9.57 (2d, 1H, J=2.1 Hz, CHO), 5.11 (t, J=7.8 Hz, 1H, $Me_2C$=$CHCH_2$), 2.51-2.35 (m, 1H, CHCHO), 2.03-1.77 (m, 2H, =$CHCH_2$), 1.70 (s, 3H, $MeCH_3C$=CH), 1.59 (s, 3H, $MeCH_3C$=CH), 1.56-1.14 (m, 3H, =$CHCH_2CHCH_2$), 1.09, 1.07 (2d, J=6.5 Hz, 3H, 2-Me), 0.89, 0.87 (2d, J=6.0 Hz, 3H, 4-Me).

$^{13}$C NMR ($CDCl_3$): δ=205.2 (d, CHO), 132.5 (s, $Me_2C$=CH), 122.5, 122.6 (2d, $Me_2C$=CH), 44.3, 44.2 (2d, CHCHO), 37.8, 37.2 (2t, $CHCH_2CH$), 35.6, 35.1 (2t, =$CHCH_2$), 31.2, 31.1 (2d, $Me_2C$=$CHCH_2$), 25.8 (q, $MeCH_3C$=CH), 19.8, 19.2 (2q, 4-Me), 17.8 (q, $MeCH_3C$=CH), 14.1, 13.3 (2q, 2-Me).

Odor description (2,4,7-trimethyloct-6-enal): citral lemongrass verbena, melon.

2) To a 100 mL three-necked flask equipped with a magnetic stirrer, a thermometer and a gas inlet, were added 2,4,7-trimethyloct-6-enal (8.00 g, 47.5 mmol) and methanol (50.0 ml). The mixture was cooled to 0° C. $NaBH_4$ was added in small portions over 20 minutes at 0° C., then the reaction mixture was warmed to room temperature and stirred for 30 minutes. Methanol was removed by rotatory evaporator. The residue was diluted with water (60.0 ml) and extracted with ethyl acetate (3×30 ml). The combined organic layers were washed with brine (10.0 mL). The organic layer was dried by $MgSO_4$, filtered and concentrated by rotatory evaporator. The crude product was purified by column chromatography (iso-hexane:ethyl acetate=10:1) followed by Kugelrohr distillation (94° C./0.10 mbar) to give 2,4,7-trimethyloct-6-en-1-ol (6.00 g, 35.2 mmol, 74.1% yield) as a colorless liquid. The analytical data are identical to those of the product obtained from method A.

EXAMPLE 2: POMELO LYCHEE FRAGRANCE ACCORD

| COMPOUND/INGREDIENT | PARTS PER WEIGHT 1/1000 |
|---|---|
| Decanal | 3 |
| Bergamot oil | 100 |
| CASSYRANE (2-tert-Butyl-5-methyl-2-propyl-2,5-dihydrofuran) | 10 |
| (E)-1,1-diethoxy-3,7-dimethylocta-2,6-diene | 6 |
| THIOLIMONENE @ 10% TEC | 3 |
| Dipropylene glycol (DPG) | 154.5 |
| FLOROPAL (2,4,6-trimethyl-4-phenyl-1,3-dioxane | 16 |
| GALAXOLIDE S[2)] | 40 |
| GARDENOL (1-phenylethyl acetate) | 8 |
| Geranyl acetate | 60 |
| HEDIONE (methyl 2-(3-oxo-2-pentylcyclopentyl)acetate) | 100 |
| 3-cis-Hexenyl acetate | 10 |
| Hexyl acetate | 80 |

-continued

| COMPOUND/INGREDIENT | PARTS PER WEIGHT 1/1000 |
|---|---|
| Hexyl salicylate | 80 |
| ISORALDEINE 70 (3-methyl-4-(2,6,6-trimethyl-cyclohex-2-en-1-yl)but-3-en-2-one) | 30 |
| JAVANOL[3] | 1 |
| Lemon oil | 60 |
| Linalool | 90 |
| 2-Dodecenal @ 10% TEC | 20 |
| MANZANATE (ethyl 2-methylpentanoate) | 10 |
| Orange oil | 80 |
| PETALIA (2-cyclohexylidene-2-o-tolylacetonitrile) | 30 |
| POMAROSE (5,3,7-trimethylocta-2,5-dien-4-one) | 1 |
| RASPBERRY KETONE (4-(4-hydroxyphenyl)butan-2-one) @ 10% TEC | 4 |
| Rose oxide | 0.5 |
| TRICYCLAL (2,4-dimethylcyclohex-3-enecarbaldehyde) | 3 |
| TOTAL: | 1000 |

[1] 4,7,7-trimethyl-6-thiabicyclo[3.2.1]octane
[2] (1,3,4,6,7,8-Hexahydro-4,6,6,7,8,8-hexamethylcyclopenta[g]-2-bensopyran
[3] 1-methyl-2-[(1,2,2-trimethylbicyclo[3.1.0]hex-3-yl)methyl]cyclopropyl]methanol In the above fragrance accord 150 parts of DPG was replaced by equal quantity of a) 2,4,7-trimethyloct-6-en-1-ol; or b) 2,4,7-trimethylocta-2,6-dien-1-ol.

The addition of 15% by weight of 2,4,7-trimethyloct-6-en-1-ol enhanced the sparkling, citrus aspect of the pomelo lychee fragrance accord and reinforced the general character of the fragrance accord. In contrast, the addition of 15% by weight of 2,4,7-trimethylocta-2,6-dien-1-ol brought more floral, rosy aspects to the citrus accord.

EXAMPLE 3: MODERN FOUGÈRE FRAGRANCE ACCORD

| COMPOUND/INGREDIENT | PARTS PER WEIGHT 1/1000 |
|---|---|
| Allyl amyl glycolate | 15 |
| AMBERMAX[4] @ 10% TEC | 5 |
| AMBROFIX (dodecahydro-3a,6,6,9a-tetramethylnaphtho[2,1-b]furan | 2 |
| CYCLAL C (2,4-dimethylcyclohex-3-enecarbaldehyde) | 1 |
| DAMASCENONE (1-(2,6,6-trimethylcyclohexa-1,3-dien-1-yl)but-2-en-1-one) | 0.5 |
| Delta Damascone (1-(2,6,6-trimethylcyclohex-3-en-1-yl)but-2-en-1-one) | 1 |
| Diethyl phthalate | 9 |
| Dipropylene glycol (DPG) | 231.5 |
| Ethyl vanillin | 1 |
| EVERNYL (methyl 2,4-dihydroxy-3,6-dimethylbenzoate) | 2 |
| FLORHYDRAL ® | 3 |
| FRESKOMENTHE (2-(sec-butyl)cyclohexanone) | 30 |
| GALAXOLIDE S | 90 |
| GERANODYLE (2-(2-hydroxypropan-2-yl)-5-methylcyclohexanol) | 15 |
| HEDIONE | 50 |
| Iso E Super | 80 |
| JAVANOL | 3 |
| Lavandin oil | 20 |
| LEMONILE ® (3,7-dimethylnona-2,6-dienenitrile) | 2 |
| METHYL LAITONE (8-methyl-1-oxaspiro[4.5]decan-2-one) @ 10% TEC | 15 |
| METHYL PAMPLEMOUSSE (6,6-dimethoxy-2,5,5-trimethylhex-2-ene) | 30 |
| PHARAONE (2-cyclohexylhepta-1,6-dien-3-one) @ 10% DPG | 3 |
| PRECYCLEMONE B [5] | 15 |
| SILVIAL (3-(4-isobutylphenyl)-2-methylpropanal) | 30 |
| Terpinyl acetate (2-(4-methylcyclohex-3-en-1-yl)propan-2-yl acetate) | 90 |
| Tetrahydro linalool (3,7-dimethyloctan-3-ol) | 230 |
| TOSCANOL (1-(cyclopropylmethyl)-4-methoxybenzene) | 2 |
| Triethyl citrate (TEC) | 9 |
| UNDECAVERTOL (4-methyldec-3-en-5-ol) | 15 |
| TOTAL: | 1000 |

[4] 2-(2,2,7,7-tetramethyltircyclo[6.2.1.0](1,6)undec-4/5-en-5-yl)propan-1-ol
[5] 1-methyl-4-(4-methylpent-3-en-1-yl)cyclohex-3-enecarbaldehyde Odor Description (Above Fragrance Accord): Fresh and Clean Modern Transparent Fougère In the above fragrance accord
a) 100 parts DPG was replaced by 100 parts of 2,4,7-trimethyloct-6-en-1-ol;
b) 200 parts DPG was replaced by 200 parts of 2,4,7-trimethyloct-6-en-1-ol;
c) 100 parts DPG was replaced by 100 parts of 2,4,7-trimethylocta-2,6-dien-1-ol; or
d) 200 parts DPG was replaced by 200 parts of 2,4,7-trimethylocta-2,6-dien-1-ol.

The addition of 10% by weight of 2,4,7-trimethyloct-6-en-1-ol brought well perceivable freshness, respecting overall fougère character whereas the addition of 10% by weight of 2,4,7-trimethylocta-2,6-dien-1-ol shifted the odor character to floral rosy, distorting the initial odor profile.

The addition of 20% by weight of 2,4,7-trimethyloct-6-en-1-ol brought well perceivable freshness, respecting overall fougère character whereas the addition of 20% by weight of 2,4,7-trimethylocta-2,6-dien-1-ol flattened the perfume, and shifted the character to floral rosy, losing the fresh and clean initial fougère masculine character.

EXAMPLE 4: "BLOOM" PERFORMANCE IN SHAMPOO

The fragrance accord from Example 2, and a fragrance accord wherein 150 parts of DPG were replaced by equal quantity of a) 2,4,7-trimethyloct-6-en-1-ol; or b) 2,4,7-trimethylocta-2,6-dien-1-ol were added to a shampoo base @ 0.5% by weight.

To a vessel containing 10 l warm water (about 30° C. to 32° C.), enclosed in a non-ventilated standard testing booth, 4 ml of the shampoo was added without mixing. The vessel was located 1.3 meter apart from the door of the booth. After 20 minutes a small window, which is located in the door of the testing booth was opened and the "bloom" performance was assessed by a panel of trained perfumers. Whereas for shampoo (a) an intense fresh, grapefruit "bloom" was noticed, only a weak, almost no freshness was noticed for the shampoo (b). Only a weak, almost no freshness was also noticed for the shampoo comprising the fragrance accord of Example 2 (i.e. the original fragrance accord in which DPG was not replaced) only.

EXAMPLE 5: "BLOOM" PERFORMANCE IN SHAMPOO OF 2,4,7-TRIMETHYLOCT-6-EN-1-OL ALONE

To a vessel containing 10 l warm water (about 30° C. to 32° C.), enclosed in a non-ventilated standard testing booth, 4 ml of a shampoo comprising 0.2% of 2,4,7-trimethyloct-6-en-1-ol/2,4,7-trimethylocta-2,6-dien-1-ol was added without mixing. The vessel was located 1.3 meter apart from the door of the booth. After 20 minutes a small window, which is located in the door of the testing booth was opened and the "bloom" performance was assessed by a panel of trained perfumers. The panelists have been asked to assess the "bloom" intensity on a intensity scale from 0 to 5 (0: not perceivable 1: very weak 2: weak 3: medium 4: strong 5: very strong). The results are shown below.

| Ingredient | "bloom" intensity | description |
| --- | --- | --- |
| 2,4,7-trimethyloct-6-en-1-ol | 3.7 | more sparkling citrus sharp, grapefruit rhubarbe |
| 2,4,7-trimethylocta-2,6-dien-1-ol (comparison) | 2.5 | More sweet |

As can be seen from the results above the compound of the present invention (2,4,7-trimethyloct-6-en-1-ol) possesses a significant higher bloom.

The invention claimed is:

1. 2,4,7-Trimethyloct-6-en-1-ol.

2. A fragrance composition or a perfumed product comprising 2,4,7-trimethyloct-6-en-1-ol.

3. The fragrance composition or perfumed product according to claim 2 further comprising an additional fragrance ingredient.

4. The composition or product according to claim 3 wherein the additional fragrance ingredient is a fragrant alcohol.

5. The composition or product according to claim 4 wherein the fragrant alcohol is selected from dihydromyrcenol, linalool, ethyl linalool, and mixtures thereof.

6. The composition or product according to claim 4 wherein the fragrant alcohol is selected from 2,4,7-trimethylocta-2,6-dien-1-ol, [1-methyl-2(5-methylhex-4-en-2-yl)cyclopropyl]-methanol, 2-(2-methyl-2-(3-methylbut-2-en-1-yl)cyclopropyl)propan-1-ol, and (2-(1-(2,2-dimethylcyclopropyl)propan-2-yl)-1-methylcyclopropyl)methanol, and mixtures thereof.

7. The product according to claim 3, wherein the product is selected from fine perfumery, fabric care, household products, beauty and personal care products and air care products.

8. The fragrance composition according to claim 3, comprising up to 30% by weight of 2,4,7-trimethyloct-6-en-1-ol based on the fragrance composition.

9. A method of imparting freshness and cleanness to a perfumed product, said method comprising the step of incorporating 2,4,7-trimethyloct-6-en-1-ol into said perfumed product.

10. The method according to claim 9, wherein up to 30% by weight of 2,4,7-trimethyloct-6-en-1-ol, based on the perfumed product, e.g. fine perfumery, laundry and fabric care, household products, beauty and personal care products and air care products, is incorporated.

11. The method according to claim 9, wherein at least 0.001% by weight of 2,4,7-trimethyloct-6-en-1-ol, based on the perfumed product, e.g. fine perfumery, laundry and fabric care, household products, beauty and personal care products and air care products, is incorporated.

* * * * *